US007688215B2

(12) United States Patent
Vokey et al.

(10) Patent No.: US 7,688,215 B2
(45) Date of Patent: Mar. 30, 2010

(54) MOISTURE DETECTION SENSOR TAPE AND PROBES TO DETERMINE SURFACE MOISTURE AND MATERIAL MOISTURE LEVELS

(75) Inventors: David E. Vokey, Sidney (CA); Gamal Mustapha, Winnipeg (CA); Jason Teetaert, Vancouver (CA)

(73) Assignee: Detec Systems LLC, Sidney, British Columbia (CA)

( * ) Notice: Subject to any disclaimer, the term of this patent is extended or adjusted under 35 U.S.C. 154(b) by 353 days.

(21) Appl. No.: 11/679,673

(22) Filed: Feb. 27, 2007

(65) Prior Publication Data
US 2008/0204259 A1  Aug. 28, 2008

(51) Int. Cl.
G08B 21/00 (2006.01)
G01N 21/00 (2006.01)
(52) U.S. Cl. .................. 340/604; 340/601; 340/602; 340/605; 73/1.02
(58) Field of Classification Search .......... 340/604–605
See application file for complete search history.

(56) References Cited

U.S. PATENT DOCUMENTS

| 4,502,044 | A | | 2/1985 | Farris | |
|---|---|---|---|---|---|
| 5,081,422 | A | | 1/1992 | Shih | |
| 5,557,263 | A | * | 9/1996 | Fisher et al. | 340/605 |
| 5,568,128 | A | * | 10/1996 | Nair | 340/573.5 |
| 6,144,209 | A | | 11/2000 | Raymond | |
| 6,175,310 | B1 | | 1/2001 | Gott | |
| 6,373,395 | B1 | * | 4/2002 | Kimsey | 340/602 |
| 6,377,181 | B1 | | 4/2002 | Kroll | |
| 6,559,772 | B2 | * | 5/2003 | Zand et al. | 340/604 |
| 7,271,729 | B2 | * | 9/2007 | Rice | 340/602 |
| 7,394,391 | B2 | * | 7/2008 | Long | 340/573.5 |

FOREIGN PATENT DOCUMENTS

| CA | 2520202 | 1/2006 |
|---|---|---|
| GB | 2235535 | 3/1991 |
| WO | WO2005010837 | 2/2005 |

* cited by examiner

*Primary Examiner*—Daniel Wu
*Assistant Examiner*—Pameshanand Mahase
(74) *Attorney, Agent, or Firm*—Adrian D. Battison; Ade & Company Inc.

(57) ABSTRACT

A moisture detection sensor is used in a building structure to detect moisture penetration. The sensor is a flat adhesive tape of a substrate of dielectric, hydrophobic material. Three or four elongate, parallel, conductors are secured to the top surface and a protective layer of non-hygroscopic, water pervious material is secured over two of the conductors so that they are exposed to surface moisture. One or two of the conductors are covered by an insulating layer to prevent moisture access. Pairs of moisture probes along the length of the tape penetrate the insulating layer, the respective conductors and the substrate and to extend into a building component to which the substrate has been adhered. A diode guide arrangement allows a monitoring unit to monitor the exposed conductors for surface moisture and the penetrated conductors for moisture in the component by reversing polarity of the voltage across the conductors.

16 Claims, 2 Drawing Sheets

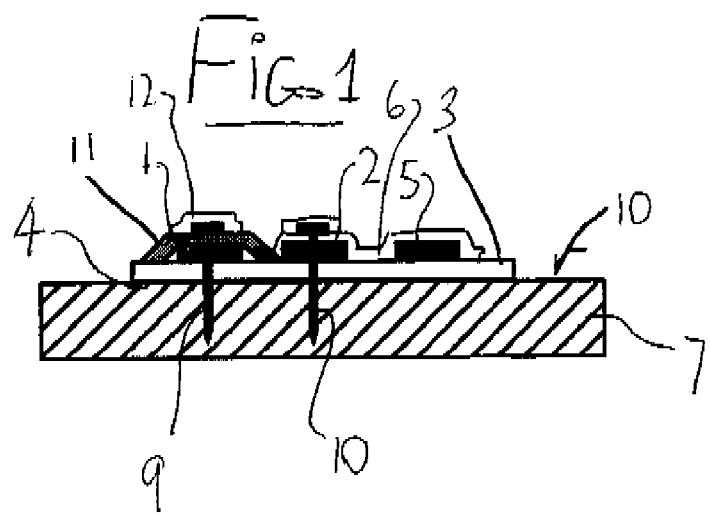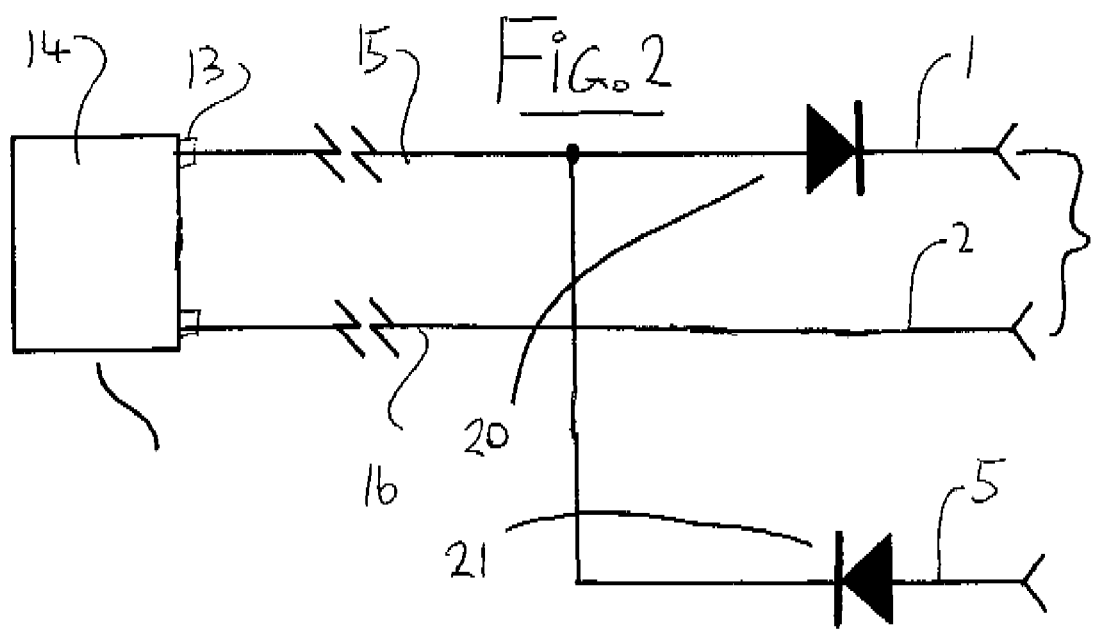

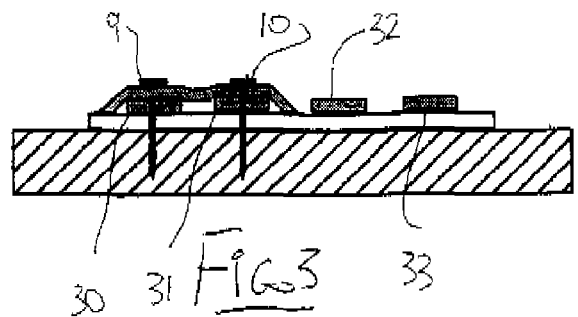
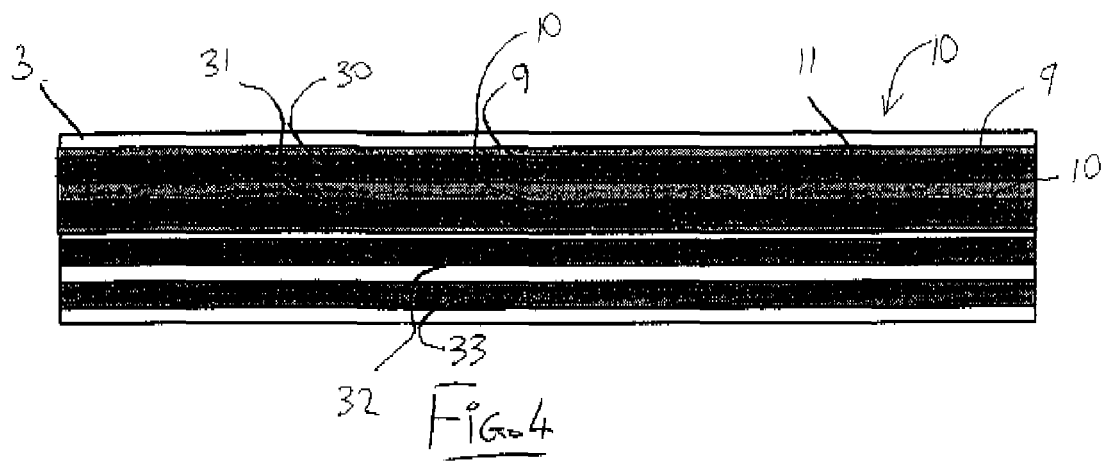
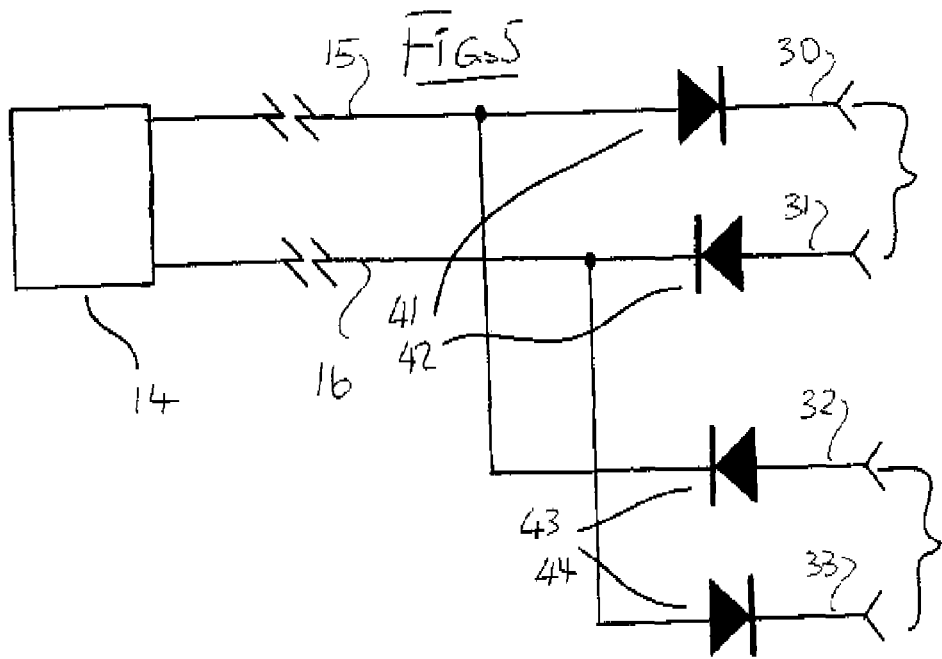

MOISTURE DETECTION SENSOR TAPE AND PROBES TO DETERMINE SURFACE MOISTURE AND MATERIAL MOISTURE LEVELS

FIELD OF THE INVENTION

The present invention relates to method for the detection of moisture penetration into and on or across the surface of materials and particularly but not exclusively to the detection of the penetration of moisture into residential and commercial structures such as in the walls or roof of a building.

BACKGROUND OF THE INVENTION

Water intrusion into buildings is a massive and growing problem. Leaking buildings cost homeowners, commercial property owners and property insurers hundreds of millions of dollars every year. Even the smallest leaks that channel water into building walls can cause expensive problems. Structural damage to plywood sheathing and stud walls due to wood rot has been commonplace for decades. Black mold or toxic mold that grows in the wet walls is known to cause severe physical problems for occupants as well as severe fiscal problems for builders and insurance companies.

Early detection and location of building envelope penetration will allow the builder or owner to identify developing problems and carry out minor repairs. These homeowners, builders, and insurance companies can avoid high costs resulting from extensive structural damage, health problems, insurance claims and potential lawsuits There are several types of moisture detection sensors available for detecting water leaks.

In U.S. Pat. No. 6,175,310 (Gott) issued Jan. 16, 2001 there is disclosed an arrangement which uses exposed conductors on a tape of a hygroscopic material where the current across the conductors is detected to detect moisture enveloping the tape.

In U.S. Pat. No. 6,377,181 (Kroll) issued Apr. 23, 2002 there is disclosed an arrangement which uses probes which are each connected to a conductor pair communicating with a central monitor which issues an alarm when moisture above a threshold is detected.

In U.S. Pat. No. 6,144,209 (Raymond) issued Nov. 7, 2000 there is provided an arrangement which describes a location method using a combination of specially designed insulated and detection conductors cabled together in a form helix. This design while useful for detection and location of water on floor like surfaces can not be placed between the roof deck and waterproof membrane because of the large overall dimensions and the susceptibility of the cable design to crushing and shorting.

U.S. Pat. No. 4,502,044 (Farris) issued Feb. $26^{th}$ 1985 discloses a plurality of sensor elements defined by side by side pairs of conductors which are adapted to be mounted in two walls of a building and which connect to a central control unit. The control unit uses a transistor which acts to detect when voltage across a resistor reaches a value sufficient to turn on the transistor to emit an alarm signal.

British Patent Application 2,235,535 (Stewart) published 1991 discloses a plurality of sensor elements defined by tapes 3 which are mounted in walls of a building and connect to a central control unit in the form of a leak detection U.S. Pat. No. 5,081,422 (Shih) issued Jan. $14^{th}$ 1992 discloses in general a plurality of moisture sensor elements each defined by a side by side pairs of conductors which have a resistance characteristic which varies in relation to a moisture content. Shih also discloses the use of probes which are connected to the wires and are driven into the material on which the wires are attached.

The present Applicants also disclose arrangements in Published PCT Application WO/05/10837 published Feb. 3, 2005. These arrangements use detection tapes and probes are suited for detecting water intrusion in selected areas of a building structure. Also in U.S. application Ser. No. 11/229, 312 filed Sep. 19, 2005 entitled "A MOISTURE DETECTION SENSOR TAPE WITH LEAK LOCATE", which corresponds to Canadian application Serial No: 2,520,202 filed Sep. 19, 2005, is disclosed an improved tape using four conductors which allow a location process to be used to locate the position of the leak along the tape. The disclosures of the above application of the present Applicant are incorporated herein by reference or may be reviewed for further details not disclosed herein.

SUMMARY OF THE INVENTION

It is an object of the present invention to provide a method of moisture detection.

According to the invention there is provided a method of detecting moisture in an absorbent material, the method comprising:

providing a tape formed by a substrate of dielectric, hydrophobic material, a layer of a mounting adhesive on a rear surface of the substrate and at least three spaced apart, elongate, generally parallel conductors mounted on a front surface of the substrate and extending therealong;

attaching rear surface of the tape by the adhesive on to a surface of the material so as to mount the conductors on the surface of the material;

engaging into the surface of the material a pair of conductive probes such that each of the conductive probes penetrates the surface of the material and engages into the absorbent material;

electrically connecting each of the probes to a respective one of the conductors;

at least one of the conductors of the tape being covered with a moisture impermeable covering material such that the at least one covered conductors is prevented from engagement with surface moisture on the tape;

two of the of the conductors of the tape being exposed to engagement with surface moisture on the tape;

applying a voltage across the two conductors which are electrically connected to the probes and monitoring currents passing between the connected conductors so as to detect changes in resistance between the connected conductors caused by moisture in the material changing the resistance between the probes;

and applying a voltage across the two exposed conductors and monitoring currents passing between the two exposed conductors so as to detect changes in resistance between the exposed conductors caused by surface moisture on the tape.

Separating surface moisture measurements from material moisture levels is of critical importance in the analysis of building envelope and roof performance. The arrangement described hereinafter overcomes the limitations of the current art by providing a method to separate and measure surface moisture and material moisture levels over a common moisture sensor and measuring circuit.

In a preferred method, the probes are electrically connected to the respective conductors by penetrating each of the respective conductors with a respective one of the pair of conductive probes as it penetrates the surface of the material and engages into the absorbent material However other arrangements for providing an electrical connection can be used including a connecting wire which is clipped to or soldered to the conductor.

Preferably the exposed conductors of the tape are covered by a protective layer of non-hygroscopic, water pervious, dielectric material secured to the top surface of the substrate and extending over the conductors. This covering layer is preferable to protect the conductors while allowing the contact of the moisture with the conductors. It also can act to collect the moisture and hold it in electrical connection across the conductors. It can also act to diffuse the moisture over the area.

In one example there are three active conductors where one of the connected conductors is exposed to the surface moisture and one of the connected conductors is covered so that one of the conductors acts in both the expose pair and the connected probe pair. Preferably this arrangement is used where there are only three conductors.

In another arrangement there are four conductors such that two of the conductors are covered and electrically connected with a respective one of the probes and two of the conductors are exposed to surface moisture.

Preferably each of the conductors is a flat metal strip at least 6.5 mm wide.

Preferably the exposed conductors are spaced apart by a distance of at least 13 mm.

Preferably each probe is a rigid elongate conductive element of corrosion resistant material which is forced into the material longitudinally of the element.

In the prime use of the method of the present invention, the absorbent material is a moisture permeable element of a building construction. However the arrangements described herein can be used in other materials and fields.

Preferably the absorbent material with the tape thereon and the probes therein is covered by a sheet material defining a component of the building construction.

Preferably the probes each have a head which is covered by a moisture impermeable covering material such as a piece of insulating tape or a bead of an insulating material.

In many cases the method includes providing a plurality of pairs of conductive probes, penetrating each pair into the absorbent material at respective spaced locations along the length of the tape and electrically connecting the pairs of probes to the connected conductors at the location.

In accordance with another aspect of the invention the conductors of the tape are connected to a monitoring unit, which applies the voltages and receives the current, by a coupling cable which includes only two conductors, wherein the monitoring unit is preferably arranged to reverse the polarity of the voltage applied to the two conductors and wherein there is provided at least one diode for guiding the applied voltage to either the exposed conductors for detecting surface moisture or to the connected conductors for detecting the moisture in the material depending on the polarity of the applied voltage.

The arrangement described herein thus overcomes the limitations of the current art by providing a novel and economic method to individually measure surface moisture and material moisture levels over the same measuring circuit. Separating surface moisture measurements from material moisture levels has been found to be of significant importance in the analysis of building envelope and roof performance.

The arrangement thus includes a first pair of measuring conductors mounted on an insulating substrate in an arrangement that provides for the detection of surface moisture and a second pair of measuring conductors mounted on the insulating substrate to measure moisture content in the subject material at selected probed locations. In one form of the arrangement, the second pair of conductors may be formed using a combination of a single conductor mounted adjacent to the first pair of conductors whereby the single conductor is used in conjunction with one of the first pair conductors to form a second probed measuring arrangement.

In a first method, an elongated, dual mode, moisture detection sensor is constructed of four parallel copper conductors laminated to an insulating substrate. A first pair of conductors is arranged such that moisture on the surface of the substrate can contact and form a conduction path between the conductors of the first pair. The conduction path is detected by a resistance measuring circuit thereby detecting the presence of moisture. The second pair of parallel conductors is constructed with an insulating layer covering the conductors such that surface moisture can not form a conductive path across the pair.

Adjacent moisture probe pairs are inserted through the insulated conductor pairs and into the absorbent material at selected locations. Electrical contact to the conductor pair is made as the probes are inserted through the insulated conductors and into the absorbent material.

In a second method, an elongated, dual mode, moisture detection sensor is constructed of three parallel copper conductors laminated to an insulating substrate. A first pair of conductors is arranged such that moisture on the surface of the substrate can contact and form a conduction path between the conductors of the first pair. The conduction path is detected by a resistance measuring circuit thereby detecting the presence of moisture. A second parallel conductor circuit is constructed by applying an insulating layer to a third conductor which is then used in combination with a single conductor of first pair to form a surface insulated pair. Adjacent moisture probe pairs are inserted through the conductors and into the absorbent material at selected locations. Electrical contact to the conductor pair is made as the probes are inserted through the insulated conductors and into the absorbent material.

For both the first and second methods, the moisture probe heads can be surface insulated by a covering of insulating tape or insulating compound.

With the addition of a diode steering circuit, both the surface and probe resistance measurements can be carried out separately over a single pair of test leads. The circuit provides individual measurement of the first pair and the second conductor pair or circuit by application of a first and second polarity. In a first polarity, the diodes allow measurement of the first conductor pair by allowing the test voltage to be applied to the conductors while blocking measurement of the second pair or circuit.

In a second polarity the diodes allow measurement of the second conductor pair or circuit by allowing the test voltage to be applied to the conductors while blocking measurement of the first pair.

BRIEF DESCRIPTION OF THE DRAWINGS

In the accompanying drawings, which illustrate an exemplary embodiment of the present invention:

FIG. 1 is an end elevational view of a tape to be used in a method according to the present invention with three conductors laminated to a base dielectric substrate which is attached by adhesive to a material to be monitored for moisture.

FIG. 2 is a schematic illustration of a monitoring unit and circuit for monitoring the resistance of the conductors of the tape of FIG. 1.

FIG. 3 is an end elevational view of a second embodiment of tape to be used in a method according to the present invention with four conductors laminated to a base dielectric substrate which is attached by adhesive to a material to be monitored for moisture.

FIG. 4 is a top plan view of the tape of FIG. 3.

FIG. 5 is a schematic illustration of a monitoring unit and circuit for monitoring the resistance of the conductors of the tape of FIG. 1.

DETAILED DESCRIPTION

Referring to FIG. 1, there is illustrated a moisture detection tape 10 constructed by applying a non-water soluble adhesive 4 to a 40 mm wide×0.1 mm thick polyvinyl chloride substrate 3. Three 0.1 mm thick×6.6 mm wide soft bare copper strips 1, 2 and 5 are laid down on the adhesive coated substrate with a 13.6 mm edge-to-edge separation. A non-hygroscopic, non-woven, water pervious layer 6 is applied over the polyvinyl substrate 3 and the copper conductors 1, 2 and 5. The non-water soluble adhesive layer 4 is applied to the underside of the polyvinyl substrate 3 and is selected such that will adhere to common building materials such as wood, steel, concrete, etc. indicated at 7. A 40 mm wide×0.1 mm thick peel off release layer (not shown) is applied over the underside adhesive layer 4, prior to its removal to expose the adhesive for application of the tape to the component 7.

When the tape is installed on a moisture absorbent building element 7, for example wood, moisture probes 9 and 10 in pairs at spaced positions along the tape are inserted through two of the detection tape conductors at critical point-locations. The probes are constructed of stainless or copper-clad steel. The probes are of a dual prong design and can be inserted with a standard construction-stapling tool.

The conductor 1 is covered by an insulating layer 11 which is impervious to moisture so that the conductor 1 is protected from contact with any surface moisture.

The heads of the probes 9 and 10 which are exposed above the conductors are covered by a piece of insulating tape or a patch of insulating material as indicated at 12.

The probes form a moisture level measurement system. The electrical resistance between the probes, which are inserted parallel to one another in the two flat conductors, varies in proportion to the moisture content in the wood material at the location of the probe. By carefully selecting the probe dimensions, distance apart and depth of insertion, the measured resistance can be used to calculate the percent moisture content in the wood. This provides a noninvasive method to effectively and continuously monitor moisture levels. Unacceptably high moisture content levels, that would otherwise go undetected with a surface moisture detection method, are readily detected.

Typically up to ten pairs of moisture probes may be inserted on a single section of detection tape. The parallel resistance of the probes can then be measured remotely by a pair of conductors 15 and 16 as shown in FIG. 2 that are spliced to the end of the detection tape and terminated on a pair of input terminals 13 of a sensor device 14 that measures the resistance of the probe combination.

In FIGS. 1 and 2 there are only three conductors where the conductors 2 and 5 form a first pair which are exposed to surface moisture since they are bare or are covered by the moisture permeable layer 6. The conductors 1 and 2 form a second pair where the insulating layer 11 over the conductor 1 prevents the second pair being responsive to surface moisture since no current can pass to the conductor 1 due to its covering layer and hence no current can pass between the conductors 1 and 2 due to surface moisture. However both conductors 1 and 2 are penetrated by the probes 9 and 10 and hence this second conductor pair is responsive to the current flowing between the probes due to the presence of moisture in the material.

The moisture level in the material can thus be detected by applying a voltage across the two conductors 1 and 2 which are electrically connected to the probes and monitoring currents passing between the connected conductors so as to detect changes in resistance between the connected conductors caused by moisture in the material changing the resistance between the probes.

The surface moisture level can thus be detected by applying a voltage across the two exposed conductors and monitoring currents passing between the two exposed conductors so as to detect changes in resistance between the exposed conductors caused by surface moisture on the tape.

In FIGS. 1 and 2 there are three active conductors where the conductor 5 is exposed to the surface moisture and the conductor 1 is covered by an insulating layer so that the conductor 2 acts in both the exposed pair for detecting surface moisture and the probe pair for detecting moisture in the material.

As shown in FIG. 2 the conductors of the tape are connected to the monitoring unit 14, which applies the voltages and receives the current, by a coupling cable which includes only two conductors 15 and 16. The monitoring unit 14 is arranged to reverse the polarity of the voltage applied to the two conductors 15 and 16 and there is provided a pair of diodes 20 and 21 for guiding the applied voltage to either the exposed conductors 2 and 5 for detecting surface moisture or to the probe conductors 1 and 2 for detecting the moisture in the material depending on the polarity of the applied voltage. Thus a positive voltage applied to the conductor 15 with a negative voltage applied to the conductor 16 acts to cause a voltage to be applied across the conductors 1 and 2 to monitor current across the probes. Reversing the polarity acts to apply the voltage across the conductors 2 and 5 to monitor surface moisture In FIGS. 3 and 4 there are four conductors 31, 32, 33 and 34 such that two of the conductors 31 and 32 are covered and electrically connected with a respective one of the probes 9 and 10 and two of the conductors 32 and 33 and bare and thus are exposed to surface moisture. Thus the two sets of conductors are separate and there is no conductor which is used for both surface and material moisture.

In FIG. 5 the same concept of diode switching is used but in this case there are four diodes 41, 42, 43 and 44 so that the voltage is switched between the conductors 30 and 32 depending on the polarity of the voltage on the line 15 and the voltage is switched between the conductors 31 and 33 depending on the polarity of the voltage on the line 16.

For use on roofs, all insulating, water pervious materials and adhesives are selected to withstand roof membrane application temperatures of 200° C. or greater for periods of several minutes or longer.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of detecting moisture comprising:
   detecting moisture within an absorbent material of a moisture permeable element of a building construction;

and detecting surface moisture on an exposed surface of the absorbent material of the moisture permeable element of the building construction by:

providing a tape formed by a substrate of dielectric, hydrophobic material, a layer of a mounting adhesive on a rear surface of the substrate and three spaced apart, elongate, generally parallel conductors mounted on a front surface of the substrate and extending therealong;

attaching a rear surface of the tape by the adhesive on to the exposed surface of the material so as to mount the conductors on the exposed surface of the material;

providing a plurality of pairs of conductive probes arranged at respective spaced locations along the length of the tape;

at each spaced location, engaging into the absorbent material through the exposed surface of the absorbent material the respective pair of conductive probes such that each of the respective pair conductive probes penetrates the exposed surface of the absorbent material and engages into the absorbent material;

electrically connecting each of the respective pair of probes to a respective one of the three conductors such that two conductors of the three conductors of the tape are connected to a respective one of the pair of probes and one of the three conductors is free from connection to the probes;

one only of the two conductors of the three conductors of the tape being covered with a moisture impermeable covering material;

such that said one covered conductor of the three conductors of the tape is prevented from engagement with said surface moisture on the tape;

and such that two of the of the three conductors of the tape exposed to engagement with said surface moisture on the tape;

applying a voltage across the two connected conductors of the three conductors of the tape which are electrically connected to the pairs of probes and monitoring currents passing between the connected conductors so as to detect changes in resistance between the connected conductors caused by said moisture within the material changing the resistance between the pairs of probes;

and applying a voltage across the two exposed conductors of the three conductors of the tape and monitoring currents passing between the two exposed conductors so as to detect changes in resistance between the exposed conductors caused by said surface moisture on the exposed surface of the absorbent material migrating onto the tape.

2. The method according to claim 1 wherein the probes are electrically connected to the respective connected conductors of the three conductors of the tape by penetrating each of the respective connected conductors with a respective one of the pair of conductive probes as the respective probe penetrates the exposed surface of the material and engages into the absorbent material.

3. The method according to claim 1 wherein the exposed conductors of the three conductors of the tape are covered by a protective layer of non-hygroscopic, water pervious, dielectric material secured to the top surface of the substrate and extending over the exposed conductors.

4. The method according to claim 1 wherein each of the three conductors of the tape is a flat metal strip at least 6.5 mm wide.

5. The method according to claim 1 wherein the exposed conductors of the three conductors of the tape are spaced apart by a distance of at least 13 mm.

6. The method according to claim 1 wherein each probe is a rigid elongate conductive element of corrosion resistant material which is forced into the absorbent material longitudinally of the element.

7. The method according to claim 1 wherein each of the probes of the pairs of probes each have a head which is covered by a moisture impermeable covering material.

8. The method according to claim 1 including providing a monitoring unit which applies the voltages and receives the current, wherein the conductors of the tape are connected to the monitoring unit by a coupling cable which includes only two conductors, wherein the monitoring unit is arranged to reverse the polarity of the voltage applied to the two conductors and wherein there is provided at least one diode for guiding the applied voltage to either the exposed conductors for detecting said surface moisture or to the connected conductors for detecting the moisture within the material depending on the polarity of the applied voltage.

9. A method of detecting moisture comprising:

detecting moisture within an absorbent material of a moisture permeable element of a building construction;

and detecting surface moisture on an exposed surface of the absorbent material of the moisture permeable element of the building construction by:

providing a tape formed by a substrate of dielectric, hydrophobic material, a layer of a mounting adhesive on a rear surface of the substrate and tour spaced apart, elongate, generally parallel conductors mounted on a front surface of the substrate and extending therealong;

providing a plurality of pairs of conductive probes arranged at respective spaced locations along the length of the tape;

a first two of the four conductors being arranged for connection to the pairs of probes for detecting said moisture within the absorbent material and a second two of the four conductors being arranged for detecting said surface moisture;

attaching a rear surface of the tape by the adhesive on to the exposed surface of the material so as to mount the conductors on the exposed surface of the material;

at each spaced location, engaging into the absorbent material through the exposed surface of the absorbent material the respective pair of conductive probes such that each of the respective pair conductive probes penetrates the exposed surface of the absorbent material and engages into the absorbent material;

electrically connecting each of the respective pair of probes to said first two of the conductors such that said first two conductors are connected to a respective one of the pair of probes and said second two of the conductors are free from connection to the probes;

said first two conductors of the conductors of the tape being covered with a moisture impermeable covering material such that said first two conductors are prevented from engagement with said surface moisture on the tape;

said second two of the conductors of the tape being exposed to engagement with said surface moisture on the tape;

applying a voltage across the first two conductors of the tape and monitoring currents passing between the first two conductors so as to detect changes in resistance between the first two conductors caused by said moisture within the material changing the resistance between the pairs of probes;

and applying a voltage across the second two conductors of the tape and monitoring currents passing between the second two conductors so as to detect changes in resistance between the second two conductors caused by said surface moisture on the exposed surface of the absorbent material migrating onto the tape.

10. The method according to claim 9 wherein the probes are electrically connected to the first two conductors by penetrating each of the respective first two conductors of the tape with a respective one of the pair of conductive probes as the respective probe penetrates the exposed surface of the material and engages into the absorbent material.

11. The method according to claim 9 wherein the second two conductors of the tape are covered by a protective layer of non-hygroscopic, water pervious, dielectric material secured to the top surface of the substrate and extending over the second two conductors.

12. The method according to claim 9 wherein each of the conductors of the tape is a flat metal strip at least 6.5 mm wide.

13. The method according to claim 9 wherein the second two conductors of the tape are spaced apart by a distance of at least 13 mm.

14. The method according to claim 9 wherein each probe is a rigid elongate conductive element of corrosion resistant material which is forced into the absorbent material longitudinally of the element.

15. The method according to claim 9 wherein each of the probes of the pairs of probes has a head which is covered by a moisture impermeable covering material.

16. The method according to claim 9 including providing a monitoring unit which applies the voltages and receives the current, wherein the conductors of the tape are connected to the monitoring unit by a coupling cable which includes only two connector conductors, wherein the monitoring unit is arranged to reverse the polarity of the voltage applied to the two connector conductors and wherein there is provided at least one diode for guiding the applied voltage to either the second two conductors for detecting said surface moisture or to the first two conductors for detecting the moisture within the material depending on the polarity of the applied voltage.

* * * * *